United States Patent [19]

Kinanen et al.

[11] Patent Number: 4,852,134
[45] Date of Patent: Jul. 25, 1989

[54] METHOD AND APPARATUS FOR RADIOGRAPHY OF THE DENTAL, JAW, AND SKULL REGIONS

[75] Inventors: Ilmari Kinanen, Espoo; Heikki Kanerva; Erkki Tammisalo, both of Turku, all of Finland

[73] Assignee: Orion-Yhtymä Oy, Helsinki, Finland

[21] Appl. No.: 10,821

[22] Filed: Feb. 4, 1987

[30] Foreign Application Priority Data

Feb. 4, 1986 [FI] Finland ................................. 860510

[51] Int. Cl.$^4$ .............................................. A61B 6/14
[52] U.S. Cl. ........................................ 378/38; 378/21; 378/39; 378/148; 378/204
[58] Field of Search ................. 378/21, 22, 27, 38–39, 378/99, 145, 147–148, 204–206; 358/111

[56] References Cited

U.S. PATENT DOCUMENTS

| | | | |
|---|---|---|---|
| 2,120,729 | 6/1938 | Chaussé | 378/205 |
| 4,145,613 | 3/1979 | Bunch | 378/27 |
| 4,221,971 | 9/1980 | Burger | 378/148 |
| 4,229,656 | 10/1980 | Iversen et al. | 378/206 |
| 4,426,726 | 1/1984 | Cheetham | 378/206 |
| 4,609,940 | 9/1986 | Born et al. | 378/205 |
| 4,646,335 | 2/1987 | Tammisalo et al. | 378/38 |
| 4,665,540 | 5/1987 | Kinnert | 378/27 |
| 4,694,478 | 9/1987 | Delnon | 378/38 |

FOREIGN PATENT DOCUMENTS

| | | |
|---|---|---|
| 2558042 | 6/1977 | Fed. Rep. of Germany ...... 358/111 |
| 790555 | 2/1979 | Finland . |
| 840412 | 2/1984 | Finland . |
| 840413 | 2/1984 | Finland . |
| 0755272 | 8/1980 | U.S.S.R. ................................. 378/39 |
| 0862916 | 9/1981 | U.S.S.R. ................................. 378/21 |
| 0791275 | 2/1958 | United Kingdom ................ 378/204 |

Primary Examiner—Craig E. Church
Assistant Examiner—John C. Freeman
Attorney, Agent, or Firm—Birch, Stewart, Kolasch & Birch

[57] ABSTRACT

A method and an apparatus for the radiographic recording of a patient's dentition, jaws, and skull regions involves seating a patient in a patient chair (9) so as localize the patient in the coordinate system of the radiographic apparatus in an unequivocal position before taking the exposure for a radiograph (87). Furthermore, in accordance with the invention, the radiograph (87) is used for measuring the coordinates of a desired object (95) by a coordinate locator (88), after which the desired partial area (94 or 96) is selected on the basis of the coordinates, and the exposure direction is changed in relation to the first exposure in the horizontal plane and/or the vertical plane before executing the exposure program for the desired partial area (94 or 96). The apparatus in accordance with the invention comprises a coordinate locator (88) which provides for locating a desired detail (95) in the panoramic radiograph in relation to the coordinate system of the radiographic apparatus, and controllers (61, 65, 67) which steer the actuators of the radiographic apparatus in a manner which implements the recording of the desired detail. By the method, a desired detail of a radiograph can be recorded in several different projections for closer examinations.

11 Claims, 7 Drawing Sheets

METHOD AND APPARATUS FOR RADIOGRAPHY OF THE DENTAL, JAW, AND SKULL REGIONS

The present invention relates to a method for the radiography of the dental, jaw, and skull regions.

The invention also concerns an apparatus for the implementation of the method.

DESCRIPTION OF THE BACKGROUND ART

Prior art methods for the radiography of the dental, jaw, and skull regions, such as the intraoral radiography, panoramic tomography, as well as the linear and polydirectional tomographies, visually perform the alignment of the recording field and object layer onto the patient only on the basis of the external structures of the patient only on the basis of the external structures of the patient by means of light beam markers, which indicate the central ray of the X-ray beam and the location of the object layer. In intraoral radiography, however, the selection of the object region is done purely on the basis of visual inspection. In addition, the different regions to be radiographed by using the aforementioned techniques are recorded on separate films.

Such panoramic equipment, which is most generally used for extraoral radiography of the jaws and the dentition onto a moving film by means of a thin, rotating X-ray beam, are also capable of recording the entire radiographed object onto a single sheet of film. A facility of recording a partial image of the object has only been possible by stopping the exposure. However, any advantage from stopping the exposure is only gained in a situation where the exposure has been started from such a part of the object which is of primary interest. In principle, it has also been possible to delineate the X-ray beam so as to expose, for instance, only the upper jaw with the upper teeth or the lower jaw with the lower teeth, onto the upper or lower part of the film sheet while shielding the lower or upper part of the film from exposure, respectively. In addition, these apparatuses employ fixed equipment specific projections in both the horizontal and vertical directions.

Also known in the art is a radiographic apparatus (FI patent application No. 79 0555), in which a part of the film sheet is used for recording the dental arch while the rest of the film is used for recording the temporo-mandibular joint in a predetermined image plane.

Panoramic radiography apparatuses known in the art are not capable of changing the projection in order to optimize the recording of an anatomic detail or for solving a diagnostic problem involving the detail. In practice, this often leads to excessively comprehensive exposures and poor radiographic hygienics relative to the task, as well as to promoting a relaxed acceptance of limited diagnostic information even if the solution to the problem is known to require the object to be recorded in several projections. In addition, the localization of the desired object to be recorded is cumbersome, or may be impossible, with the use of prior art panoramic radiography equipment.

SUMMARY OF THE INVENTION

The aim of the present invention is to overcome the drawbacks of the aforementioned prior art technology and to provide a novel method for the radiography of the regions of dentition, jaws and skull.

The invention is based on dividing the panoramic imaging area into predetermined partial exposure areas, which are partly overlapping and cover the entire radiographed area, with the apparatus adapted so as to allow a desired detail of the panoramic image to be recorded by identifying a partial area with a localizer from the panoramic image, and then radiographing only the desired partial area in two minimum projections.

More specifically, the invention is characterized by placing a patient in a patient chair, exposing a first radiographic image by moving the X-ray source and X-ray film by a stepping member, measuring the coordinates of a desired object, selecting an exposure area based on those coordinates, altering an imaging direction in respect to the first exposure, moving various elements to implement an exposure sequence, recording the selected exposure area at least once using a predetermined sequence of movements and recording the selected exposure area a second time if required by altering the imaging direction.

The present invention offers substantial benefits, the most important of which involves avoidance of the need to localize the radiographic object during the radiography session or to base the localization on visual criteria. Also, the possible verifications of the image region and layer against the radiographed object can be performed in a controlled manner because the starting coordinates of the previous image are known. Another important advantage of the invention is the appreciable level of freedom in the combination of image program sequences utilizing the entire film area. On the other hand, separated regions of the upper and lower parts of the object can be combined into a single recording program.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, the invention will be examined in more detail by means of the exemplifying embodiments in accordance with the attached drawings which are given by way of illustration only, and thus, are not limitative of the present invention, and wherein.

DETAILED DESCRIPTION OF THE PREFERRED EMBODIMENTS

Figure 1:
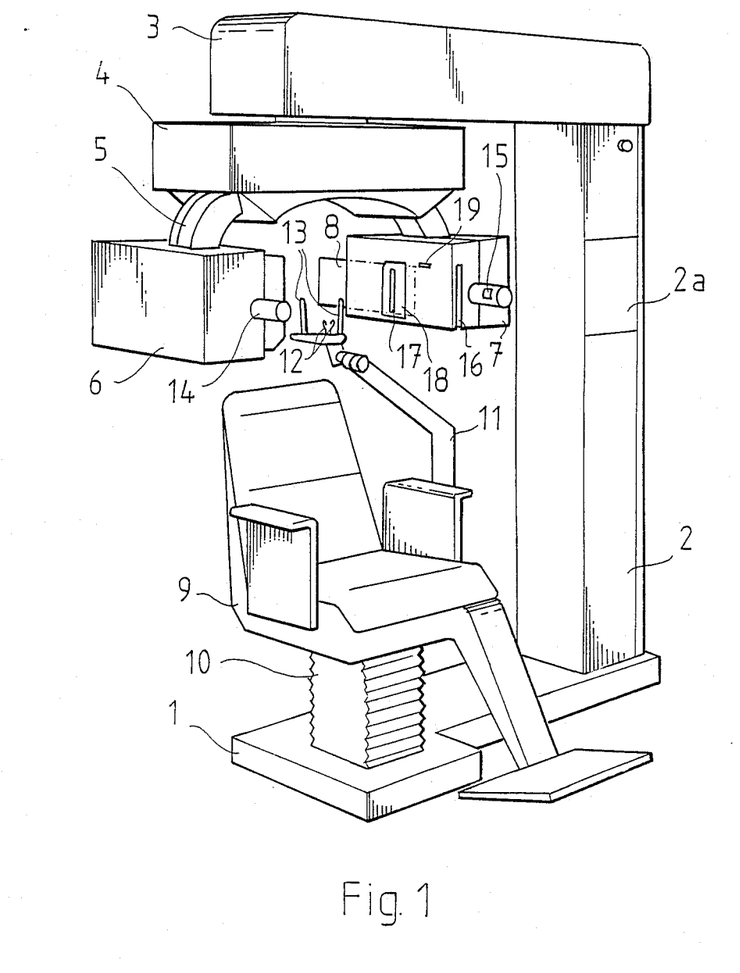
FIG. 1 shows a perspective view of the basic parts of the radiographic apparatus.

FIG. 1 shows the basic components of the radiographic apparatus. A floor-mounted base 1 supports a frame unit of the apparatus comprising a hollow-core column 2 and a horizontal beam 3. The beam 3 carries a rotating section 4, connected to the beam by means of a vertical shaft. Further, the rotating section 4 carries an arch-formed curved beam 5 so as to allow the curved beam to glide in a circular motion relatively to the aforementioned rotating section. The other end of the curved beam 5 carries a generator head 6 which contains, among other things, an X-ray tube. The opposite end of the curved beam carries a cassette head 7, containing a radiographic film cassette 8 for image recording.

Furthermore, the base 1 supports a patient chair 9, which can be elevated or lowered by means of a lift actuator 10 in relation to the base 1. The chair 9 is attached to the lift actuator 10 via a linear actuator (not shown in FIG. 1), by means of which the chair can be shifted forward and backward in relation to the base 1. In addition, a patient positioner 11 is attached to the chair 9 so as to allow the positioner elevation to be adjusted in relation to the chair according to the height of the patient (positioner actuator not shown in FIG. 1). The upper end of the positioner 11 carries a patient jaw support 12 and side supports 13, which align the jaws on the center line and hold them immobilized during the exposure.

FIG. 1 also shows the light marker projectors 14 and 15 for patient positioning, a gliding slot 16 for the film cassette 8, secondary collimator blinds, or openings 17 and 18 for the X-ray beam together with a selector device 19 connected mechanically to the blinds.

For the recording of desired kinds of radiographic images, the exemplified embodiment provides totally eight degrees of freedom of movement or setting, each provided with a separate electronically controlled electric motor. In the following, the aforementioned degrees of freedom are listed in short:

1. Horizontal rotation: the rotation of the rotating section 4 in relation to the vertical shaft attached to the beam 3.
2. Vertical rotation: the movement of the curved beam 5 in relation to the rotating section 4.
3. X-axis movement: the linear movement of the rotation shaft of the rotating section 4 in relation to the longitudinal axis (X-axis) of the beam 3.
4. Y-axis movement: the linear movement of the chair 9 (and the patient) in the forward-backward direction (Y-axis).
5. Film movement in relation to the X-ray beam: the linear movement of the film cassette 8 in relation to the cassette head 7 within the gliding slot 16.
6. Radial movement: the linear movement of the rotating section 4 along its longitudinal axis (in the plane determined by the curved beam) in relation to the rotation shaft attached to the beam 3.
7. Z-axis movement: the vertical linear movement of the chair 9 (and the patient) in relation to the base by means of the lift actuator 10.
8. Setting movement of the primary collimator: the setting movement which sets the X-ray collimator slit in the generator head 6, and consequently, delineates the X-ray beam size.

Figure 2:
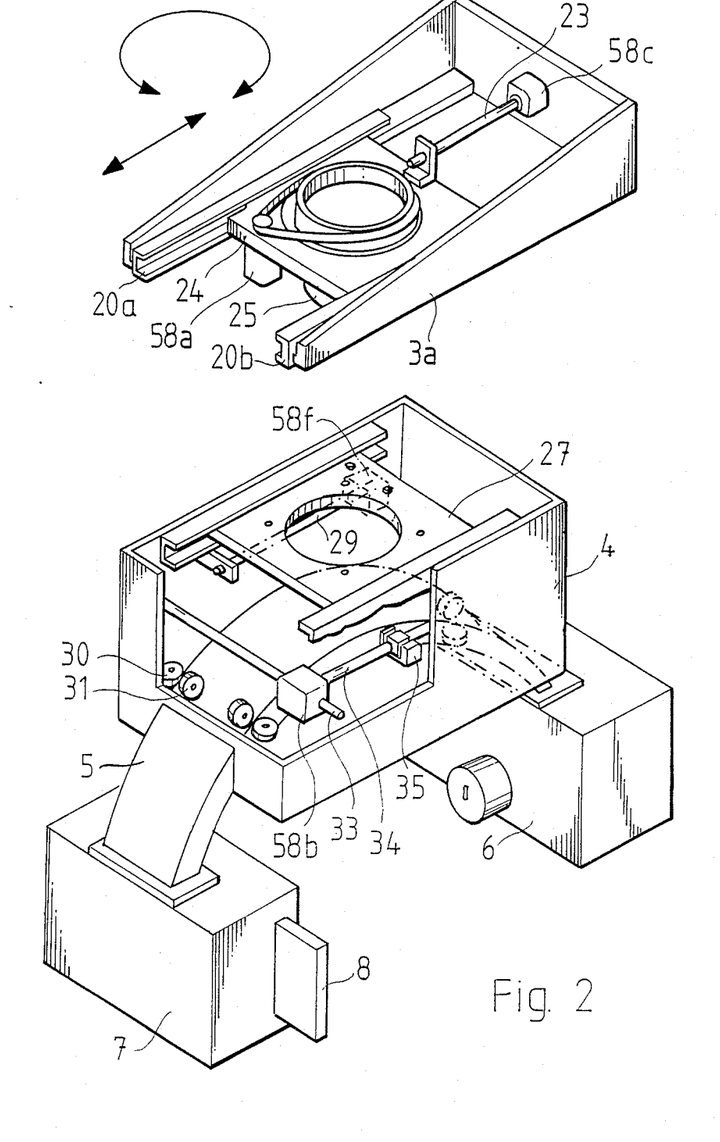
FIG. 2 shows the details of the actuators attached to the base unit.

FIG. 2 shows details of the embodiments of actuators attached to the base unit of the radiographic apparatus. This figure is principally similar to that described in the FI patent applications Nos. 84 0412 and 84 0413. In regard to the horizontal and vertical rotations and the radio movement, FIG. 2 serves the same purposes as described in the aforementioned patent applications. In comparison, the actuator performing the X-movement in the aforementioned application fulfills the same function in image recording which in this invention has been achieved by means of the Y-movement in FIG. 2.

A support member 3a is shown in FIG. 2 as an integral part of the beam 3 shown in FIG. 1. Guided by slotted rails 20a and 20b, which are attached to the support member 3a, is a transfer plate 24 adapted movable by a motor 58c via a drive screw 23. This transfer movement corresponds to the X-movement defined above. The transfer plate 24 carries on bearings a pivotally connected vertical rotation shaft 25, which is rotated by a motor 58a. Further, the shaft 25 is connected to a transfer plate 27, which is moved relative to a rotating section 4 by a motor 58f via a drive screw 29. This movement corresponds to the radial movement defined above. Also shown in FIG. 2 is a curved beam 5 connected to the rotating section 4, which cooperates with rolls 30 and 31, mounted on bearings inside the rotating section 4 and resting against the side, upper, and lower surfaces (the latter not shown) of the curved beam, thus guiding the beam along its own curvature. The transfer movement, or the vertical rotation movement defined above, is effected on the beam by means of a linear actuator motor 58b, mounted pivotally on bearings by a shaft 33 to the rotating section 4, with its threaded shaft 34 connected to a counter piece 35, pivotally mounted to the side of the curved beam.

The horizontal movement of the chair 9 (Y-movement) is advantageously implemented with a similar construction as shown in FIG. 2 for the movement of the transfer plate 24.

In principle, any similar conventional construction of the art as used in, for instance, dentist's chairs, is as suitable as the lift actuator 10 of the chair 9. Advantageously applicable is such a construction in which the actuator is an electric motor, such as a stepping motor.

A plurality of conventional constructions, described e.g. in patent publications, is applicable for moving the film cassette 8 with an electric motor driven actuator. An advantageously applicable mechanism has, for instance, such a construction in which a drive screw, like screws 23, 29, and 34 in FIG. 2, moves a carrier in the film cassette gliding slot, into which the cassette can be inserted and withdrawn. A preferable construction of the cassette carrier has one end left open. Then, only a horizontal movement is required to insert and withdraw the cassette.

Figure 3:
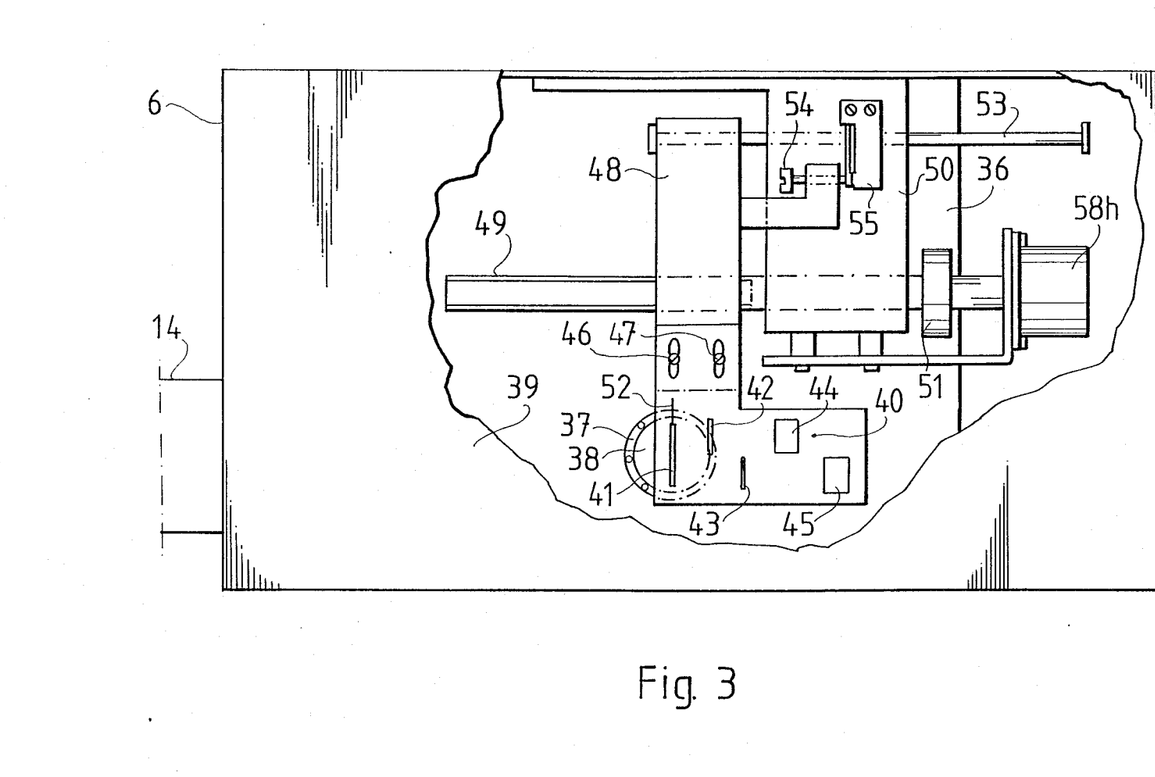
FIG. 3 shows the construction of the components of the primary collimator.

FIG. 3 shows the construction of the primary collimator inside a generator head 6 as viewed from the direction of the cassette head 7. A metal box 36, located rearmost in the generator head enclosure, contains the actual X-ray tube, the insulation oil, high-voltage parts, etc. A front panel 39 of the enclosure has an X-ray window 38, mounted with an annular flange 37. Located immediately behind the generator head front panel 39 is a collimator slit plate 40 which has several collimator slits 41, 42, 43, 44, 45. The collimator plate is constructed of a material possessing an effective X-ray absorption. It can be moved by an electronic control into a position in which a desired collimator slit is very accurately and symmetrically located with respect to the horizontal axis 52 of the X-ray window. The purpose of different collimator slits is to delineate a desired size of an X-ray beam to a desired height onto the radiographic film sheet. The slit 41 forms a narrow beam extending from the upper edge of the film to the lower edge. Slits 42 and 43 also form a narrow beam which extends to only half of the film sheet height so as to expose the upper part of the film by slit 42 and the lower part by slit 43. Slits 41, 42, and 43 are intended for narrow-slit exposures, while the broader slits 44 and 45 are applicable for layer imaging by tomography.

FIG. 3 also shows the actuators, which make the desired movements and positioning of the collimator slit plate 40 possible. The slit plate 40 is mounted to a carriage 48 with screws 46 and 47, which provide a vertical adjustment. This carriage has a horizontal threaded hole, inside which a drive screw 49 rotates, thus imparting a horizontal movement to the carriage 48 and, consequently, also the slit plate 40. A base member 50, permanently mounted to the generator head enclosure, serves as the frame of the entire collimator assembly. The drive screw 49 is rotatably mounted via a bearing (not shown) to the base member 50, in order to eliminate the axial play. The drive screw 49 is provided with a flywheel 51, and finally, connected to the shaft of a stepping motor 58h. The rotation of the carriage 48 is inhibited by a rod 53 attached to the carriage and adapted to glide through the base member 50. The sideways position of the slit 41 is adjustable by a screw 54, which cooperates with a limit switch 55, connected to the control circuit of a motor 58h. After the aforementioned basic adjustment, any other collimator slit is also accurately aligned because the stepping motor 58h precisely steps a predetermined distance for each control pulse.

The aforementioned description dealth with the mechanical implementation of each of the eight degrees of freedom of actuators and settings. A preferred actuator for each degree of freedom is a stepping motor which is characterized by the movement of an exact angle increment of the motor shaft rotation per each control pulse. The desired rotation speed is achieved by feeding the motor with an appropriate stepping pulse rate. Correspondingly, a desired distance of transfer (rotation angle) is obtained by feeding a certain number of pulses. Both control conditions are advantageously implemented using digital techniques and microprocessor technology.

Figure 4:
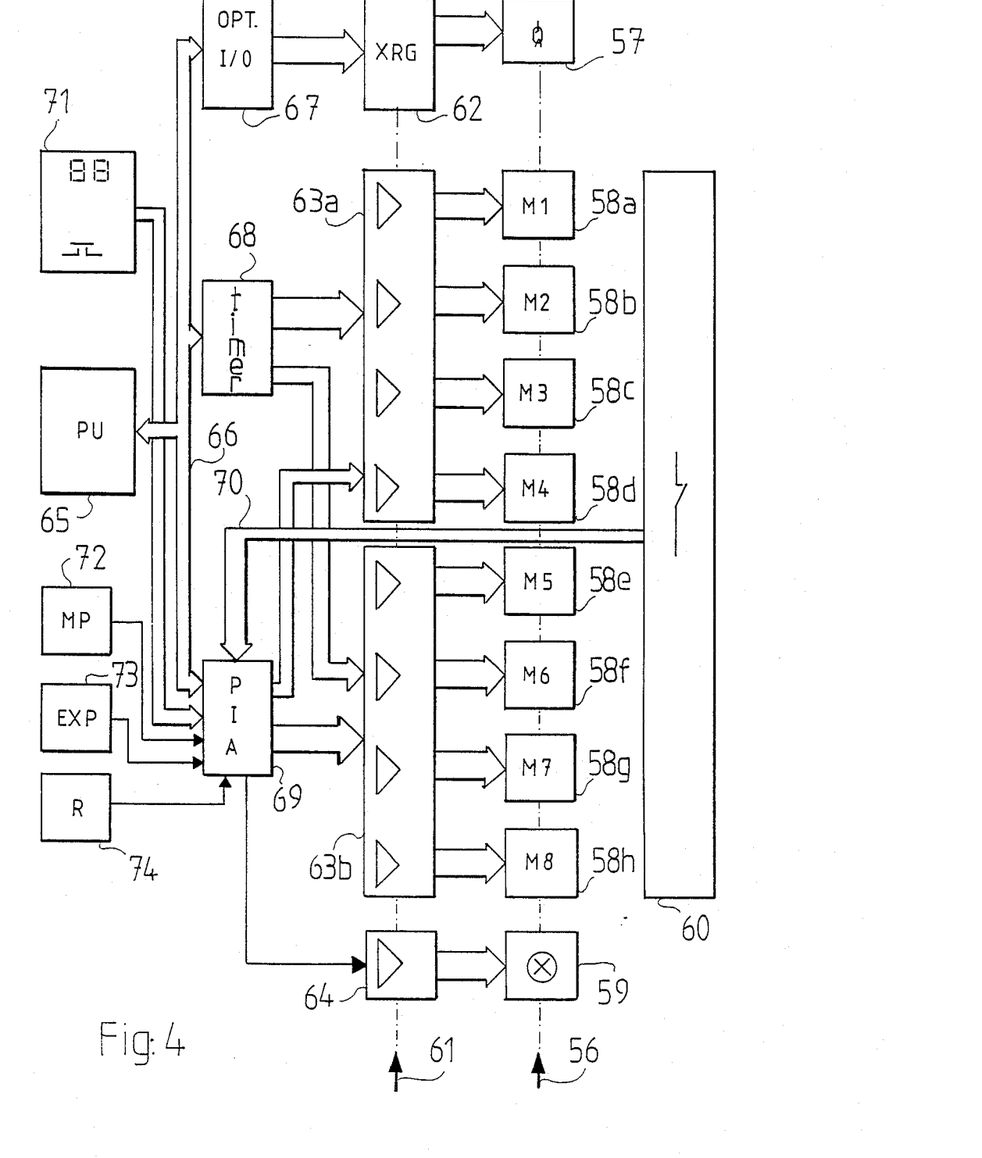
FIG. 4 shows the block diagram of control electronics for the actuator and setting members.

FIG. 4 shows the electronic block diagram of the functional controls of the radiographic apparatus. For the sake of clarity, the block diagram omits the connections of power supplies to different units. The actuators proper are shown by a vertical line 56. An X-ray source proper 57 incorporates an X-ray tube which is located in the enclosure 36 of the X-ray source head 6. The actuators 58a . . . 58h of mechanical movements are stepping motors, which have been described previously in conjunction with the description of degrees of freedom of movements and settings. Light sources 59 are incorporated in light marker projectors 14 and 15. Limit switches 60 cooperate with the movement and setting members driven by the stepping motors; an exemplifying case of a limit switch 55 being shown in FIG. 3.

A vertical line 61 indicates the circuits, which feed the electric power to the actuators in proper formats for each actuator and at appropriate time instants. An X-ray generator 62 incorporates circuits that feed the anode and heater power to the X-ray tube 57, so as to provide a desired emission of radiation at desired time instants. Pulse circuits 63a and 63b incorporate a total of eight identical circuits, each of which feeds the corresponding stepping motor with a pulse rate determined by the input signal. A light marker controller 64 incorporates a power switch, which switches the operating voltage to lamps 59 when the input signal is activated.

The other blocks shown in FIG. 4 incorporate the actual input and logic units of the radiographic apparatus. A central role is played by a processing unit 65 (PU = Processing Unit), which, in addition to incorporating the actual microprocessor or central processing unit, also contains other circuits, such as a clock circuit and several memory and interface circuits. The memory circuits of the processing unit provide a permanent storage for the basic operating logic of the radiographic equipment, or the operating system, and for the operating sequence commands associated with the different exposure programs.

In the actual operation of the radiographic apparatus, the processing unit 65 communicates via a main communications bus 66 with an interface unit 67 (Opto-Coupled Input/Output Circuit) of the X-ray generator, a pulse rate generator unit 68 of the stepping motors, and an interface unit 69 (Parallel Interface Adapter) of general functional commands. The latter unit receives return information of the operational states of mechanical members via a bus 70.

The input devices comprise a display and selector panel 71, which is situated at a location 2a of the column; pushbuttons 72 (Manual Positioning) for manually controlled movements, a pushbutton 73 (Exposure) for recording, or exposing; and a pushbutton 74 (Return) for resetting.

The following description details the operation of units shown in FIG. 4 in different operating conditions with the purpose of exemplifying the functions incorporated in some of the units.

A return program is started in the processing unit 65 by pushing the reset button 74 which returns all movement and setting members to their starting positions. An important function in this operation is provided by limit switches 60, which inform from the positions of different movement members. A uniquely determined starting position is assigned the rotating section 4, the curved beam 5, the film cassette 8, the radial position (transfer plate 27), and the primary collimator plate 40. The operating system ensures that the exposure cannot be started unless the aforementioned members are in their starting positions.

After resetting the apparatus to the starting position by pushbutton 74 and seating the patient in the chair 9, pushbuttons 72 are operated to perform the alignment setting for the patient, which is described later in detail. In regard to the operation of the movement members, the patient alignment setting means that the patient is aligned to an appropriate position in respect to the coordinate system of the radiographic apparatus by adjusting under manual control the X-movement (transfer plate 24), the Y-movement (horizontal movement of chair) and the Z-movement (vertical movement of the chair) until the desired situation is achieved.

The selection and display panel 71 incorporates pushbuttons for the selection of variables associated with the exposure settings (anode current, anode voltage, exposure rate) and the desired exposure program. The display part of the panel incorporates digital displays, which indicate the selected anode voltage, anode current, number of selected exposure program together with the associated exposure time. In addition, the display incorporates indicator lights that indicate the readiness of the apparatus for exposure and the energization of the X-ray generator.

When the situation is completely prepared for an exposure, the exposure is started by pushing the button 73 continuously. Then, the exposure program, which is selected from the selector panel 71, is started with the entire chain of functional sequences being performed according to commands stored in the ROM memory of the processing unit 65. When the exposure program has been executed or if the button 73 is released before the execution is completed, all exposure functions are stopped. A new exposure is possible only after returning the apparatus to the starting state by pushing the button 74 (Reset).

Figure 5:
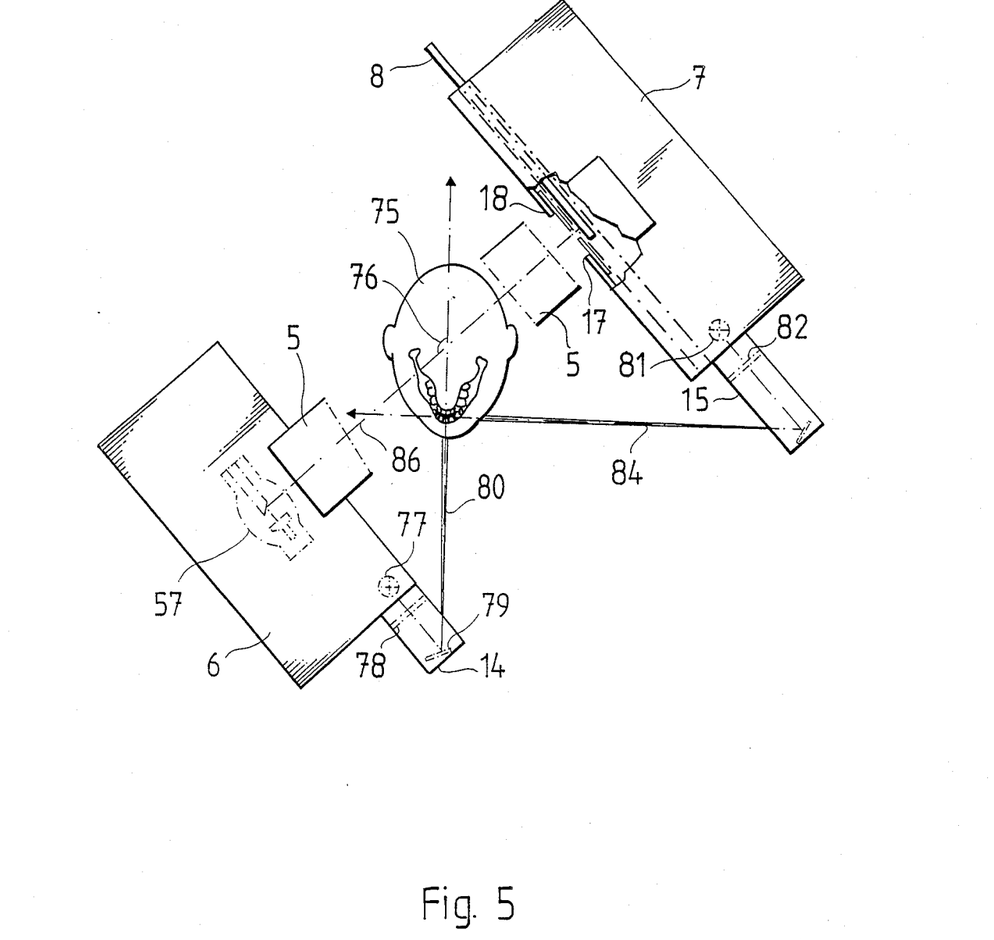
FIG. 5 shows the arrangements of patient alignment.

The foregoing description concerning FIG. 4 incurred a reference to patient alignment setting by buttons 72. FIG. 5 depicts the coordinate system and light marker adaptations associated with the patient alignment setting. In the figure, the mutual relationships of the patient 75 and the radiographic apparatus are shown in top view and in the starting condition of the exposure. Then, the symmetry plane 86 of the curved beam 5 and a vertical plane passing through the Y-axis form a known intersect angle 76 with each other. A light marker projector 14, which is incorporated in the generator head 6, comprises a light source 77, a slit collimator 78, and a mirror 79. The light collimator 78 includes components for generating a narrow, collimated light line onto the patient's face. In the horizontal direction, a narrow light beam 80 coincides with the fixed Y-axis relatively to the radiographic apparatus. Correspondingly, a light marker projector 15 integrated in the cassette head 7 incorporates a light source 81, a slit collimator 82, and a mirror 83. In the horizontal direction, a narrow light beam 84 coincides with the X-axis of the radiographic apparatus, which is perpendicular to the aforementioned Y-axis. The collimator also incorporates a horizontal slit which projects to the left side of the patient's head a horizontal light line defining a fixed basic Z-plane relatively to the X-ray imaging members. In this manner, the light marks generated by the combinations of light marker generators 14 and 15 define a fixed X-Y-Z coordinate system in respect to the radiographic apparatus.

Furthermore, a fixed coordinate system with respect to the patient can be defined as follows: Let the X'-axis pass via the region of the patient's front teeth roots from left to right; and correspondingly, let the Y'-axis pass in the sagittal plane of the patient from front to back. The purpose of the patient alignment setting is to make the X-Y and X'-Y' coordinate systems coincide as shown in FIG. 5. In practice, this is achieved as follows: by operating the X-movement under manual control, the light beam 80 is aligned to coincide with the sagittal plane of the patient (center line of face). By operating the Y-movement of the chair, the patient chair (together with the patient) is adjusted to a position in which the light beam 84 marks the roots of the front teeth. By operating the Z-movement of the chair, the horizontal light line of member 15 is adjusted to mark the jaws at a height at which the radiographic image is to be exposed or at a height which is desired to be used as the starting position of exposure. With the help of side supports 13 depicted in FIG. 1, the patient's head is aligned to a position in which the Y and Y' axes are parallel. The described situation is now called the basic alignment positioning of the patient.

FIG. 5 also shows how the central ray of the X-ray beam emitted from the X-ray tube 57 coincides with the center point of the secondary collimator openings 17 and 18 in the cassette head 7. By operating a selector member 19 shown in FIG. 1, the metal plate associated with the collimator opening 17 is pushed aside when such exposure programs are used in which the X-ray beam size is defined by the collimator slits 44 or 45 of FIG. 4.

In radiographic examinations performed by using the panoramic apparatus described herewith, the first or basic exposure is the panoramic radiography of the dentition and jaws. Numerous patent publications describe how the image is formed in this method. However, some basic facts are valuable and should be described herewith. The following description refers to the previously elucidated diagrams, FIG. 5 in particular. In the panoramic radiography, the X-ray beam size is determined by the collimator slit 41 shown in FIG. 3. The image formation is determined by two basic factors: the first factor is governed by the manner in which the central ray 86 of the X-ray beam intersects the dental arch and the jaw bone during each phase of the exposure. In this invention, the projection is determined by the rotation angle of the X-ray beam (angle position of the rotating section 4) and by the Y-position of the chair. The second factor concerns the movement of the cassette 8. The velocity of this movement is programmed to be such that it retains the velocity of those image point projections of the desired image layer from within the patient which are to be recorded sharply on the film equal with the actual cassette velocity at the plane of the cassette. This means that the horizontal rotation movement of the rotating section, the Y-movement of the chair, and the movement of the cassette must retain a certain relationship with each other during every instant of the exposure.

Further, a corollary of this condition is that each position of the X-ray beam corresponds to a certain position on the film. Conversely, this means that if a position of the object image from the patient is determined on the film, also the location of this object point is known in the coordinate system of the radiographic apparatus.

Figure 6:
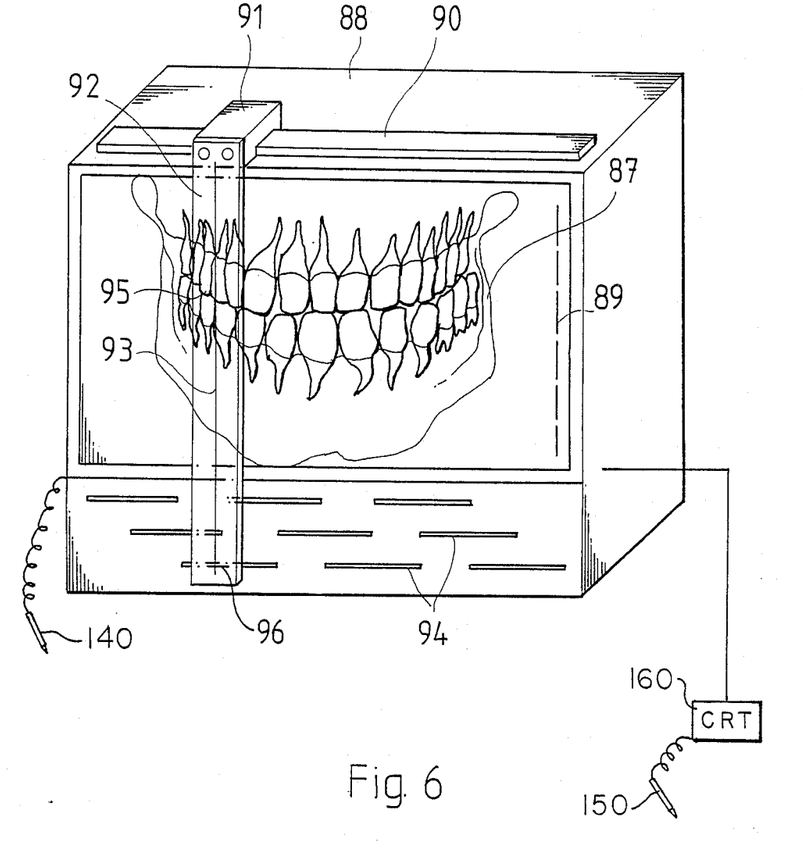
FIG. 6 shows the localizer of the radiographic object.

Related to this conclusion is the operating principle of the image object localizer shown in FIG. 6. In the figure, a panoramic radiograph 87 is laid on the surface of a radiograph viewing light table 88 so as to align the edge of the exposed area on the film with an alignment line 89 marked on the table surface. The upper rim of the light table carries a rail 90 along which a glide member 91 can be moved. A transparent strip 92 with a market line 93 moves with the glide member in front of the X-ray film. The lower part of the light table enclosure has a group of numbered lines 94, which are within the reach of the operating area of the marker line 93. Each line indicates a partial area, which is recorded with the correspondingly numbered partial exposure program. The arrangement shown in FIG. 6 is employed by aligning the marker line 93 with the partial area of desired detailed radiograph. Then, the lower part of the marking line indicates which exposure program is appropriate for recording the corresponding area. For instance, to record an area 95, an appropriate exposure program is selected corresponding to the line 96.

The object localization can also be performed by placing at the rims of the film examination area 88 a sufficiently dense matrix of light-emitting diode transmitters and photosensitive detectors so as to obtain from the transmitters mounted on two intersecting rims and the receiving detectors mounted on the opposing intersecting rims, a unique position information for a detail 95 of a radiograph 87 when pointed by, for instance, a pen 140.

The object point localizing device can also be a light pen 150, connected to a CRT display 160, which would offer an easy, program-controlled method for assigning an exposure program corresponding to the proper recording procedure for the indicated image object. However, this technique assumes the conversion of radiographic information into an appropriate format for the CRT display. While the transparent strip 92 and numbered line 94 have been indicated in FIG. 6, along with both pen 140 with its associated transmitters and detector and the CRT display 160 and light pen 150, it should be understood that only one of these localizers or any other combination thereof could be used.

When a detailed image is desired from a suspected object, for instance, the area 95 in FIG. 6, it is essential to gain additional information in respect to the information content of the panoramic image by the use of the partial area imaging. This is achieved by adapting the partial area exposure program to perform exposures in several rather than only one projection of the desired area. Another possibility which is applicable in tomography is to expose several adjacent "slices" of the same area onto the same film sheet. When the method of multiple projections is used, it is possible to change the exposure direction in the horizontal plane and/or vertical plane. Changing the exposure direction in the horizontal plane is implemented by varying the horizontal rotation movement and Y-movement. In order to change the vertical exposure angle, the position of the curved beam 5 is altered. In the latter case, it is advantageous to adapt the position of the transfer 27 (radial position) such as to make the center point of the curved beam 5 to coincide with the exposed area. Then, changing the position of the curved beam retains the image of the exposed area at same height on the film.

Partial images taken from two different directions can also be placed on the film pairwise such as to generate one or several stereo image pairs. Images of a stereo pair taken with a horizontal shift of the projection center can be placed on the film adjacently. In the case of a vertical shift of a projection center, the images of the stereo pair must correspondingly be placed above one another (one of the images to the upper part of the film, the other to the lower part) if the pair is desired to be directly observable as a stereo image.

Depending on the size of partial images and number of desired projections, a single film can be utilized for recording partial images even from several than one partial area. In this case the exposure program can be configured for a purposeful placement of partial images on the film.

Figure 7:
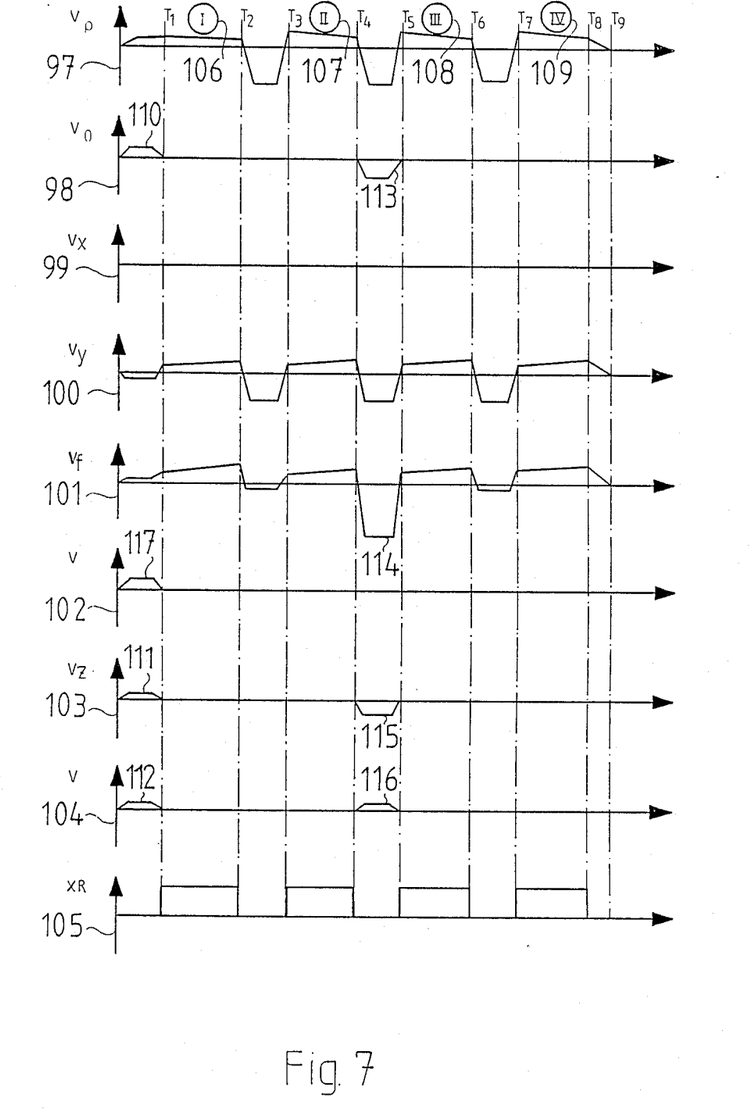
FIG. 7 shows velocity graphs of the actuator and setting members during the execution of an exposure program.

FIG. 7 shows as an example of the structure of exposure programs the velocity graphs of different movement and setting members as a function of time in such an exposure program which records from a selected partial area to the upper part of the film a horizontal stereo pair of images, and aligned with the previous pair to the lower part of the film, another horizontal stereo pair of images such as to form from the first images of the aforementioned pairs, a first pair of vertical stereo images, and from the second images, a second pair of vertical stereo images, correspondingly.

In order to examine the vertical stereo pairs of images, the film must be rotated by graph 90 so that the images, originally located above one another, will be viewed adjacently.

The different functions shown in FIG. 7 are as follows: graph 97 depicts the angle velocity ($v_{100}$) of the horizontal rotation movement; graph 98 depicts the angle velocity ($v_\theta$) of the vertical rotation movement; graph 99 depicts the velocity ($v_x$) of the X-movement; graph 100 depicts the velocity ($v_y$) of the Y-movement; graph 101 depicts the velocity ($v_f$) of the film cassette; graph 102 depicts the velocity ($v_r$) of the radial movement (transfer plate 27); graph 103 depicts the velocity ($v_z$) of the vertical movement of the chair; graph 104 depicts the velocity ($v_c$) of the primary collimator 40; and graph 105 depicts the energization (XR) of the X-ray generator.

It can be noted by studying graph 105 that the time intervals 106, 107, 108 and 109 are the actual exposure cycles. Furthermore, it is evident that only the horizontal rotation, the Y-movement, and the cassette movement are active during the exposure cycles.

With regard to the time intervals and the movements, the following can be noted: The exposure starting button is pressed and held down starting from the time instant 0. During the time interval $0 \ldots T_1$, or the initial positioning, the different members are driven to their home positions and the correct velocities of exposure apparatus movements are attained. Graph 110 illustrates the alignment of the correct vertical angle by driving the curved beam 5 to an appropriate position. Graph 117 illustrates the alignment of the curved beam center point with the area to be recorded. Graph 111 illustrates a minor raising of the patient chair since the first exposure will be recorded at the upper part of the film. Graph 112 illustrates the transfer of the collimator slit 42 in front of the X-ray window. Time interval $T_2 \ldots T_3$ is utilized for the first intermediate positioning, during which the rotating section is returned to the displacement of the desired stereo angle in respect to the position of time instant $T_1$. Correspondingly, the Y-position of the chair is returned by means of the Y-position control of the chair. By contrast, the film is transferred only by a minor advancement for the next image frame. An analogous intermediate positioning is performed during the time interval $T_6 \ldots T_7$. the two first exposure cycles (106 and 107) are utilized for recording the first horizontal stereo pair while the second pair is recorded during the exposure cycles 108 and 109. The time interval $T_4 \ldots T_5$ of intermediate positioning is different from the others. As illustrated by graph 113, the vertical angle is then altered, the film cassette is returned to the position of time interval $T_1$ (114), the chair is lowered (115), and the collimator slit 42 is replaced by the slit 43 (116). The time interval $T_8 \ldots T_9$ is utilized for decelerating the moving members to a halt.

As shown in FIG. 7, the X-movement is halted for the entire execution of the exposure program. The movement is only needed during the patient alignment setting. If the patient has left the radiographic apparatus after the panoramic image recording, a new alignment positioning of the patient to the basic position must be done according to the procedure described in conjunction with FIG. 5. The use of the localizer illustrated in FIG. 6 as an aid to the exposure program selection presumes an identical positioning of the patient relative to the radiographic apparatus in all exposure programs.

FIG. 7 illustrates an exposure program representing in principle an analogous slit exposure technique as is conventionally used for the panoramic recording of the regions of the dentition and jaws. The embodiment described herewith also facilitates the employment of tomography for the imaging of anatomic layers. The tomographic exposure mode can be used as such in two different fashions: in the case of a thin layer imaging, a series of adjacently located slice images are recorded from the same object while a thick layer can be recorded by stereo pair exposures.

The tomographic imaging technique is characterized by, among other things, the following: during the exposure, the film cassette is stationary (not moving) while the X-ray beam performs a circular or ellipsoidal rotation movement with the imaged partial area being the center point of the rotation movement. The slit imaging technique also introduces a minor tomographic effect—but only in the horizontal direction. The selection criteria between the two methods described above can be formulated as follows: slit imaging is a preferred choice when the projection center (virtual focus) is to be changed, while the tomographic recording method is appropriately chosen for blurring the undesired areas in more than one dimension.

In the foregoing, the invention has been exemplified only with reference to its preferred embodiment. The spirit of the claims to be presented also permits the consideration of other forms of embodiment, which will be described in the following.

In the above illustrations, the alignment of partial images at the upper and lower parts of the film sheet was based on the use of different locations of the primary collimator while the film is held stationary in the vertical direction. Another embodiment of the invention utilizes only a single slit or rectangle of a lesser height while a vertical positioning facility of the film cassette caters to the alignment of the X-ray beam exposing the upper or lower part of the film, respectively.

The slit imaging technique described in the foregoing utilizes the combination of the rotating section movement and the Y-movement to achieve the rotation of the X-ray beam around the momentary rotation center, or the desired projection center. With regard to the exposure, the equivalent end result can be achieved by aligning the rotation axis of the horizontal rotation with the desired rotation center during the initial positioning of the patient by means of both the Y-movement and the X-movement. Then, only the movements of the rotating section and the film cassette are required during the exposure. This alternative embodiment is applicable to the partial exposures of confined areas. The procedure is analogous to the method from the early days of slit imaging techniques, called pantomography.

Illustrated in the example shown in FIG. 6 is the panoramic X-ray image covering the areas of the dentition and jaws as a basic image by means of which the desired anatomic partial object is localized. The principle is also adaptable to other types of basic images. Another example to be noted is the examination of mandibular joints by radiography in which the first exposure is appropriately taken as an orienting panoramic image for defining the direction and orientation of the condyles in the different planes of the coordinate system.

The foregoing treaties dealt only with the radiographic imaging of the area of the dentition and jaws. The exemplified radiographic apparatus is also applicable as such in exposures of many other regions of the skull. Another potential use for the multiple projection method is in the examinations of skull fractures. As known, a bone fracture is visible on the X-ray film only if the X-ray beam happens to pass appropriately via the fracture line and perpendicular to the bone surface. This rather random coincidence can be brought under a higher level of control by exposing the suspected fracture area multiple times, each exposure being taken from a slightly altered direction. Additionally, the radiography of auditory organs may gain from the use of the apparatus described herewith.

The foregoing discussion has punctuated the stereo image pairs as examples of images taken from different directions. However, the scope of the invention is not limited to these but instead, depending on the anatomic area and the corresponding clinical practice, even other combinations of projections may be applicable. Again, an exemplifying case is the radiography of the mandibular joint condyle from which the different projections, when appropriately taken, are recorded on a single film representing the axial direction of the condyle and the images perpendicular to the axial direction.

What is claimed is:

1. A method for radiographing areas of a patient's dentition, jaws, and skull comprising the steps of:

placing the patient in a patient chair having support apparatuses for achieving a unique positioning of the patient relative to a coordinate system of a radiographic apparatus;

exposing a first radiographic image by sweeping an X-ray beam emitted from an X-ray source over a portion of the patient and synchronizing an X-ray film with the X-ray source by pulse controlled stepping members to expose said radiographic image, the X-ray beam being swept stepwise to obtain projections from desired layers to be sharply imaged over a surface of the film with an equal velocity to that of the film;

operating an object locating apparatus to select from the first radiographic image;

an exposure sequence for a desired object, said sequence has defined a number of control pulses for stepping members corresponding to said exposure sequence of said desired object, so as to alter an imaging direction with respect to the first exposure in at least one of a horizontal and vertical directions;

selectively altering a position of the patient during subsequent radiography sessions relative to the patient chair and the support apparatuses to a position used during a first radiography session;

implementing said exposure sequence by moving the X-ray source, a slit plate of an X-ray window, the X-ray film, and the patient with at least the stepping members in accordance with the exposure sequence corresponding to an area to be recorded, so as to record a selected exposure area at least once by using a predetermined sequence of movement; and selectively recording the selected exposure area a second time on the same film by altering the imaging direction.

2. The method in accordance with claim 1, wherein vertical and horizontal rotational movements of the X-ray beam are used for recording the desired object with tomographic radiography so that rotation axes of the vertical and horizontal rotational movements are arranged to intersect at an intersection point, and the intersection point coincides with the desired object and wherein a broad collimator slit is used for the exposing to be performed using an X-ray beam sweeping in a multidirectional trace over the desired object so that the desired object is at a rotation center while the X-ray film remains stationary with respect to the X-ray beam.

3. The method in accordance with claim 1 or 2, wherein the movements of the radiographic apparatus are implemented using pulse controlled stepping motors.

4. The method in accordance with claim 3, wherein an X-ray beam direction is altered relative to a first exposure in a horizontal plane by varying horizontal rotation movement and Y-movement of the patient chair by pulse controlled stepping motors.

5. The method in accordance with claim 4, wherein the X-ray beam direction is altered in a vertical plane by altering the position of a curved beam arranged on a rotational section by a pulse controlled stepping motor.

6. The method in accordance with claim 5, wherein a radial imaging position is altered by moving the rotating section with respect to a longitudinal axis by a pulse controlled stepping motor so that the exposed area remains at a constant height on the film.

7. The method in accordance with claim 1, wherein the number of control pulses corresponding to a position of the desired object are defined by conveying a glide member over the radiographic image, which has been aligned with an alignment line on a light table, and by aligning a marker line of the glide member over the desired object, after which the marker line indicates an appropriate exposure area.

8. The method in accordance with claim 1, wherein the number of control pulses corresponding to a position of the desired object are electronically determined by a CRT display and a light pen.

9. An apparatus for implementation of radiography over areas of a patient's dentition, jaws, and skull comprising:

patient positioning members with which the patient can be placed and retained during a complete exposure in a unique position with respect to a radiographic apparatus;

a movable X-ray source with a collimated X-ray beam;

a movable X-ray film holder cooperating with the X-ray source;

pulse controlled stepping members for stepwise moving the X-ray source with respect to the patient, and for stepwise moving the film holder with respect to the X-ray beam whereby a first X-ray image can be recorded;

means for determining a start position of the X-ray source and the X-ray film holder;

a first set of stepping rotation members with which a combined vertical rotation movement of the X-ray source and the film holder can be implemented for imaging of vertical radiographic projections;

a second set of stepping rotation members with which the X-ray source and the film holder are movable in a horizontal plane with respect to a vertical rotation shaft;

stepping transfer members with which a slit plate is movable with respect to an X-ray window in order to shape the X-ray beam;

a localizing apparatus comprising means for locating a desired partial object in the first X-ray image wherein said means to locate selects an exposure sequence for the desired partial object, wherein said exosure sequence has defined a number of control pulses; and control means for using the defined control pulses for controlling the pulse controlled stepping members, the first set of stepping rotation members, the second set of stepping rotation members and the stepping transfer members to take an exposure over the desired partial object.

10. The apparatus in accordance with claim 9, wherein the localizing apparatus comprises an alignment line with which the X-ray image can be aligned to a standardized place, a rail along which a glide member is movable, a transparent strip with a marker line and a numbered scale over which the marker line can be located.

11. The apparatus in accordance with claim 9, wherein the pulse controlled stepping members, the first set of stepping rotation members, the second set of stepping rotation members and the stepping transfer members are stepping motors.

* * * * *